US008912340B2

(12) United States Patent
Abele et al.

(10) Patent No.: US 8,912,340 B2
(45) Date of Patent: Dec. 16, 2014

(54) PROCESS FOR THE PREPARATION OF 2-IMINO-THIAZOLIDIN-4-ONE DERIVATIVES

(75) Inventors: Stefan Abele, Oberwil BL (CH); Martin Bolli, Allschwil (CH); Gunther Schmidt, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 205 days.

(21) Appl. No.: 13/565,469

(22) Filed: Aug. 2, 2012

(65) Prior Publication Data

US 2012/0302758 A1    Nov. 29, 2012

Related U.S. Application Data

(63) Continuation-in-part of application No. 12/516,055, filed as application No. PCT/IB2007/054752 on Nov. 22, 2007, now Pat. No. 8,263,780.

(30) Foreign Application Priority Data

Nov. 23, 2006 (WO) .................. PCT/IB2006/054409

(51) Int. Cl.
   *C07D 277/54* (2006.01)
(52) U.S. Cl.
   CPC .................................. *C07D 277/54* (2013.01)
   USPC .......................................................... 548/184
(58) Field of Classification Search
   None
   See application file for complete search history.

(56) References Cited

U.S. PATENT DOCUMENTS

| 3,077,402 | A | 2/1963 | Blout et al. |
| 3,175,905 | A | 3/1965 | Stahlhofen |
| 3,759,938 | A | 9/1973 | Giraudon |
| 5,422,360 | A | 6/1995 | Miyajima et al. |
| 5,677,322 | A | 10/1997 | Yasumura et al. |
| 6,353,006 | B1 | 3/2002 | Dixon et al. |
| 6,380,229 | B1 | 4/2002 | Yoneda et al. |
| 7,435,828 | B2 | 10/2008 | Binkert et al. |
| 7,626,037 | B2 | 12/2009 | Binkert et al. |
| 7,767,701 | B2 | 8/2010 | Hasegawa et al. |
| 7,875,726 | B2 | 1/2011 | Binkert et al. |
| 8,263,780 | B2 | 9/2012 | Abele et al. |
| 8,273,779 | B2 | 9/2012 | Binkert et al. |
| RE43,728 | E | 10/2012 | Binkert et al. |
| RE43,833 | E | 11/2012 | Binkert et al. |
| 8,524,752 | B2 | 9/2013 | Binkert et al. |
| 2004/0009527 | A1 | 1/2004 | Dong et al. |
| 2004/0167192 | A1 | 8/2004 | Solow-Cordero et al. |
| 2005/0019825 | A9 | 1/2005 | Dong et al. |
| 2005/0096364 | A1 | 5/2005 | Romine et al. |
| 2007/0082933 | A1 | 4/2007 | Binkert et al. |
| 2007/0249599 | A1 | 10/2007 | Duffy et al. |
| 2008/0146629 | A1 | 6/2008 | Binkert et al. |
| 2008/0280962 | A1 | 11/2008 | Binkert et al. |
| 2009/0275625 | A1 | 11/2009 | Binkert et al. |
| 2010/0317867 | A1 | 12/2010 | Abele et al. |
| 2011/0021581 | A1 | 1/2011 | Brossard et al. |
| 2011/0196004 | A1 | 8/2011 | Bonham et al. |
| 2012/0302612 | A1 | 11/2012 | Binkert et al. |
| 2012/0302758 | A1 | 11/2012 | Abele et al. |

FOREIGN PATENT DOCUMENTS

| EP | 1 219 612 | 7/2002 |
| GB | 999796 | 7/1965 |
| WO | WO 91/17151 | 11/1991 |
| WO | WO 96/20936 | 7/1996 |
| WO | WO 2004/007491 | 1/2004 |
| WO | WO 2004/010987 | 2/2004 |
| WO | WO 2005/054215 | 6/2005 |
| WO | WO 2006/094233 | 9/2006 |

OTHER PUBLICATIONS

U.S. Appl. No. 13/951,954, Binkert et al.
Anonymous, "Actelion's Orally Active Selective S1P1 Receptor Agonist to be Jointly Developed/Promoted with Roche in Autoimmune Disorders and Transplantation Deal Potentially Worth Well Over US $630 Million to Actelion", Muscoskeletal Report, [Online], Jul. 20, 2006, pp. 1, New York, NY 10016, USA, Retrieved from the Internet: URL: http://www.mscreport.com/print.cfm?articleID=827>.
Bailar et al; The New England Journal of Medicine; 1997; Massachusetts Medical Society, vol. 336, Issue 22, pp. 1569-1574.
Baker; Journal of Applied Physiology; 2002; American Physiological Society; vol. 92; pp. 1779-1780.
Beger et al; World Journal of Surgery; 2003; Societe Internationale de Chirugie; vol. 27; pp. 1075-1084.
Berge et al; "Pharmaceutical Salts"; Journal of Pharmaceutical Sciences; vol. 66, No. 1; 1977; pp. 1-19.
Braun-Moscovici et al; Current Opinion in Rheumatology; 2002; Lippincott Williams and Wilkins; vol. 14; pp. 711-716.
Bunemann et al; "Activation of Muscarinic K+ Current in Guinea-Pig Atrial Myocytes by Sphingosine-l-phosphate", Journal of Physiology, vol. 489, pp. 701-707, (1995).

(Continued)

*Primary Examiner* — Michael Barker
(74) *Attorney, Agent, or Firm* — Hoxie & Associates LLC

(57) ABSTRACT

The present invention relates to a new process for the preparation of 2-imino-thiazolidin-4-one compounds of the Formula (I) and (II) and to compounds of Formula (II) as such. The present compounds of Formula (II) can be used as intermediates in the preparation of thiazolidin-4-one derivatives of the General Formula (II), said derivatives being described in WO 2005/054215. These compounds of General Formula (II) are described in WO 2005/054215 to act as immunosuppressive agents.

19 Claims, No Drawings

(56) References Cited

OTHER PUBLICATIONS

Carter et al; "Photochemically enhanced Binding of Samll Molecules to the Tumor Necrosis Factor Receptor-1 Inhibits the binding of TNF-alpha"; PNAS. vol. 98, No. 21, Oct. 9, 2001; pp. 11879-11884.
Davidov et al; "Chronic Nitric Oxide Synthase Blockade Desensitizes the Heart to the Negative Metabolic Effects of Nitric Oxide", Life Sciences, Pergamon Press, Oxford, GB, vol. 79, pp. 1674-1680, (2006).
Ehrlenmeyer et al; "Structural Chemical Investigations. VII. Reactive Behavior of Thiourea to Unsaturated Acids"; CA 37:10142, 1943.
Frolkis et al; "The Role of 'Invertors' (Intracellular Activators) in Age-related Changes in Cell Response to Hormones", Experimental Gerontology, vol. 30, pp. 401-414, (1995).
Fujishiro et al; "Use of Sphingosine-l-Phosphate 1 Receptor Agonist, KRP-203, in Combination with a Subtherapeutic Dose of Cyclosporine A for Rat Renal Transplantation", Transplantation, vol. 82(6), pp. 804-812, (2006).
Gibson; "Pharmaceutical Preformulation of Formulation"; HIS Health Group, Englewood, CO, USA 2001; Table of Contents.
Giese et al; Journal of Cancer Research and Clinical Oncology; 2001; Springer-Verlag; vol. 127, pp. 217-225.
Gould et al; "Salt Selections for Basic Drugs"; Int. J. Pharm.; vol. 33; 1986; pp. 201-217.
Guo et al; "Effects of Sphingosine 1-phosphate on Pacemaker Activity in Rabbit Sino-atrial Node Cells", Pflugers Arch, vol. 438, pp. 642-648, (1999).
Hale et al; "Selecting Against S1P3 Enhances the Acute Cardiovascular Tolerability of 3-(N-benzyl)aminopropylphosphonic Acid SIP Receptor Agonists", Bioorganic & Medicinal Chemistry Letters, vol. 14(13), pp. 3501-3505, (2004).
Himmel et al; "Evidence for Edg-3 Receptor-Mediated Activation of IK.Ach by Sphingosine-l-Phosphate in Human Atrial Cardiomyocytes", Molecular Pharmacology, vol. 58, pp. 449-454, (2000).
Huwiler et al; "New Players on the Center Stage: Sphingosine 1-Phosphate and its Receptors as Drug Targets", Biochemical Pharmacology, Pergamon Press, Oxford, GB, vol. 75, pp. 1893-1900, (2008).
Janusz et al; "New Cyclooxygenase-2/5-Lipoxyfenase Inhibitors. 3. 7-tert-Butyl-2,3-dihydro-3, 3-dimethylbenzofuran Derivatives as Gastrointestinal Safe Antiinflammatory and Analgesic Agents: Variations at the 5 Position"; J. Medicinal Chemistry, vol. 41, 1998, pp. 3515-3529.
Kappos et al; "Oral Fingolimod (FTY720) for Relapsing Multiple Sclerosis", The New England Journal of Medicine, vol. 355(11), pp. 1124-1140, (2006).
Klika et al; "Regioselective Synthesis of 2-imino-1,3-thiazolidin-4-ones by Treatment of N-(Anthracen-9-yl)-N9-ehylthiourea [. . . ]" Eur. J. Org. Chem. 2002, pp. 1248-1255.
Kovarik et al; "A Mechanistic Study to Assess Whether Isoproterenol Can Reverse the Negative Chronotropic Effect of Fingolimod", Journal of Clinical Pharmacology, vol. 48, No. 3, pp. 303-310, (2008).
Koyrakh et al; "The Heart Rate Decrease Caused by Acute FTY720 Administration is Mediated by the G Protein-Gated Potassium Channel IKACh", American Journal of Transplantation, vol. 5, pp. 529-536, (2005).
Ma; "High-Affinity Activators of Cystic Fibrosis Transmembrance Conductance Regulator (CFTR) Chloride Conductance Identified by High-Throughout Screening"; The Journal of Biological Chemistry, vol. 277, No. 40, Issue of Oct. 4, pp. 37235-37241; [2002].
Martinet et al; Journal of the National Cancer Institute; 2000; National Cancer Institute; vol. 92; No. 11; pp. 931-936.
Non-Final Office Action dated Feb. 1, 2011, U.S. Appl. No. 12/516,055 [AC-76].
Ochi et al; "Sphingosine-l-Phosphate Effects on Guinea Pig Atrial Myocytes: Alterations in Action Potentials and K+ Currents", Cardiovascular Research, vol. 70, pp. 88-96, (2006).
Ottana et al; 5-Arylidene-2-imino-4-thiazolidinones: Design and Synthesis of Novel Anti-Inflammatory Agents, Biorganic and Medicinal Chemistry, 13(13) (2005) pp. 4243-4252.
Peters et al; "Sphingosine-l-Phosphate Signaling in the Cardiovascular System", Current Opinion in Pharmacology, vol. 7(2), pp. 186-192, (2007).
Remington; "The Science and Practice of Pharmacy"; 20th Edition; Philadelphia College of Pharmacy and Science; 2003; Table of Contents.
Sanna et al; "Sphingosine 1-Phosphate (SIP) Receptor Subtypes S1P1 and S1P3, Respectively, Regulate Lymphocyte Recirculation and Heart Rate", The Journal of Biological Chemistry, vol. 279(14), pp. 13839-13848, (2004).
Smith et al; Annals of Neurology; 2003; American Neurological Association; vol. 54; pp. 186-196.
Surh; Nature Reviews Cancer; 2003; Nature Publishing Group; vol. 3; pp. 768-780.
U.S. Appl. No. 14/028,712, filed Sep. 17, 2013, Binkert et al.
Ellis, et al., "Treatment of Chronic Plaque Psoriasis by Selective Targeting of Memory Effector T Lymphocytes", The New England Journal of Medicine, vol. 345, No. 4, (Jul. 26, 2001), pp. 248-255.
Notices of Allowance dated Jul. 21, 2011, Nov. 15, 2011, and May 3, 2012, U.S. Appl. No. 12/516,055 [AC-76-US].
Ottana, et al., 5-Arylidene-2-imino-4-thiazolidinones: Design and Synthesis of Novel Anti-Inflammatory Agents, Bioorganic and Medicinal Chemistry, 13 (13) (2005), pp. 4243-4252. (available online May 17, 2005).

PROCESS FOR THE PREPARATION OF 2-IMINO-THIAZOLIDIN-4-ONE DERIVATIVES

CROSS REFERENCE TO RELATED APPLICATIONS

This application is a continuation-in-part application of U.S. Ser. No. 12/516,055, filed Nov. 22, 2007, which application is a U.S. national stage application filed under 35 U.S.C. 371 of PCT/IB2007/054752, filed on Nov. 22, 2007, which claims the benefit of PCT/IB2006/054409, filed on Nov. 23, 2006, the contents of each of which are incorporated herein by reference in their entirety.

FIELD OF THE INVENTION

The present invention relates to a new process for the preparation of 2-imino-thiazolidin-4-one compounds of the Formula (I) and (II) and to compounds of Formula (II) as such. The present compounds of Formula (II) can be used as intermediates in the preparation of thiazolidin-4-one derivatives of the General Formula (II), said derivatives being described in the PCT Patent Application with the publication number WO 2005/054215. These compounds of General Formula (II) are described in WO 2005/054215 to act as immunosuppressive agents.

DESCRIPTION OF THE INVENTION

In a first aspect the present invention relates to a new process for the preparation of a compound of the Formula (I):

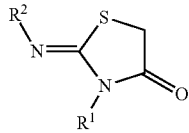

Formula (I)

wherein
$R^1$ represents phenyl which is optionally mono-, di- or tri-substituted wherein the substituents are independently selected from $C_{1-7}$-alkyl and halogen; and
$R^2$ represents $C_{1-7}$-alkyl;
which process comprises reacting a compound of the formula $R^1$—N=C=S, wherein $R^1$ is as defined for Formula (I), with a compound of the formula $R^2$—$NH_2$, wherein $R^2$ is as defined for Formula (I), followed by reaction with bromoacetyl bromide and a pyridine base.

Preferably the above process is performed without the isolation and/or purification of intermediates such as the thiourea intermediate that occurs after reacting a compound of Structure 1 with a compound of Structure 2.

Preferably the pyridine base that is used in the preparation processes described herein is pyridine, lutidine or a cholidine, preferably pyridine.

Preferably the above process is used to prepare compounds of Formula (I), wherein $R^1$ represents phenyl which is optionally mono-substituted with $C_{1-7}$-alkyl (such as especially methyl) or halogen, and $R^2$ represents $C_{1-7}$-alkyl (such as especially propyl, isopropyl or butyl).

More preferably the above process is used to prepare compounds of Formula (I), wherein $R^1$ represents phenyl which is optionally mono-substituted with methyl or chloro, and $R^2$ represents propyl, isopropyl or butyl.

Especially preferred, the above process is used to prepare compounds of Formula (I) selected from the group consisting of:
2-[(Z)-isopropylimino]-3-phenyl-thiazolidin-4-one,
3-phenyl-2-[(Z)-propylimino]-thiazolidin-4-one,
2-[(Z)-n-butylimino]-3-phenyl-thiazolidin-4-one,
2-[(Z)-isopropylimino]-3-o-tolyl-thiazolidin-4-one,
2-[(Z)-isopropylimino]-3-(3-chlorophenyl)-thiazolidin-4-one, and
2-[(Z)-propylimino]-3-o-tolyl-thiazolidin-4-one.

In a further aspect the present invention relates to a process for the preparation of a compound of Formula (II):

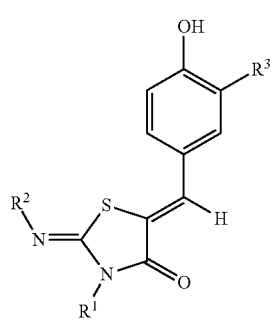

Formula (II)

wherein
$R^1$ and $R^2$ are as defined for Formula (I) above; and
$R^3$ represents hydrogen, hydroxy, $C_{1-7}$-alkoxy, or halogen;
which process comprises preparing a compound of Formula (I) according to the procedure described above and reacting such compound of Formula (I) with a compound of Structure 3:

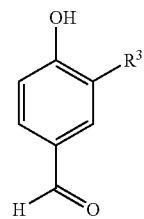

Structure 3 wherein $R^3$ is as defined for Formula (II) above.

In a preferred embodiment the present invention relates to a process for the preparation of a compound of Formula (II) as described above, wherein the compound of Formula (I) is reacted with the compound of Structure 3 in the presence of acetic acid and a base (especially sodium acetate), preferably at elevated temperatures, especially at temperatures between 40 and 80° C., preferably at 55° C. The reaction can also be carried out in a non-polar solvent such as toluene or benzene in the presence of an amine such as pyrrolidine or piperidine.

In another aspect the present invention relates to a process for the preparation of a compound of the Formula (II), wherein $R^1$, $R^2$ and $R^3$ are as defined above, which process comprises reacting a compound of the formula $R^1$—N=C=S, wherein $R^1$ is as defined for Formula (I), with a compound of the formula $R^2$—$NH_2$, wherein $R^2$ is as defined for Formula (I), followed by reaction with bromoacetyl bromide and a pyridine base, such as especially pyridine, to obtain a compound of Formula (I) (especially wherein the preparation of the compound of Formula (I)

occurs without the isolation and/or purification of intermediates), followed by reaction with a compound of Structure 3, wherein $R^3$ is as defined above, characterized in that the compound of Formula (I) is not isolated and/or purified, i.e. for example without any extractive aqueous work-up and concentration to dryness.

In a preferred embodiment the present invention relates to a process for the preparation of a compound of Formula (II) as described in the preceding paragraph, wherein the preparation of the compound of Formula (I) occurs in the presence of dichloromethane, followed by a solvent change in order that the reaction with a compound of Structure 3 occurs in the solvent acetic acid and in the presence of a base (especially sodium acetate), preferably at elevated temperatures, especially at temperatures between 40 and 80° C., preferably at 55° C. The reaction with a compound of Structure 3 can also be carried out in a non-polar solvent such as toluene or benzene in the presence of an amine such as pyrrolidine or piperidine.

Preferably the above processes are used to prepare compounds of Formula (II), wherein $R^1$ represents phenyl which is optionally mono-substituted with $C_{1-7}$-alkyl (such as especially methyl) or halogen, $R^2$ represents $C_{1-7}$-alkyl (such as especially propyl, isopropyl or butyl), and $R^3$ represents hydrogen, $C_{1-7}$-alkoxy (such as especially methoxy), or halogen.

More preferably the above processes are used to prepare compounds of Formula (II), wherein $R^1$ represents phenyl which is optionally mono-substituted with methyl or chloro, $R^2$ represents propyl, isopropyl or butyl, and $R^3$ represents hydrogen, methoxy, or chloro.

Especially preferred, the above processes are used to prepare compounds of Formula (II) selected from the group consisting of:
5-(3-chloro-4-hydroxy-benz-(Z)-ylidene)-2-[(Z)-isopropylimino]-3-phenyl-thiazolidin-4-one,
5-(3-chloro-4-hydroxy-benz-(Z)-ylidene)-2-[(Z)-propylimino]-3-phenyl-thiazolidin-4-one,
5-(3-chloro-4-hydroxy-benz-(Z)-ylidene)-2-[(Z)-butylimino]-3-phenyl-thiazolidin-4-one,
5-(3-chloro-4-hydroxy-benz-(Z)-ylidene)-2-[(Z)-isopropylimino]-3-(o-tolyl)-thiazolidin-4-one,
5-(3-chloro-4-hydroxy-benz-(Z)-ylidene)-2-[(Z)-isopropylimino]-3-(3-chloro-phenyl)-thiazolidin-4-one,
5-(3-chloro-4-hydroxy-benz-(Z)-ylidene)-2-[(Z)-propylimino]-3-(o-tolyl)-thiazolidin-4-one,
5-(4-hydroxy-benz-(Z)-ylidene)-2-[(Z)-propylimino]-3-phenyl-thiazolidin-4-one,
5-(4-hydroxy-3-methoxy-benz-(Z)-ylidene)-2-[(Z)-propylimino]-3-phenyl-thiazolidin-4-one,
5-(4-hydroxy-benz-(Z)-ylidene)-2-[(Z)-butylimino]-3-phenyl-thiazolidin-4-one,
5-(4-hydroxy-3-methoxy-benz-(Z)-ylidene)-2-[(Z)-butylimino]-3-phenyl-thiazolidin-4-one,
5-(4-hydroxy-benz-(Z)-ylidene)-2-[(Z)-propylimino]-3-(o-tolyl)-thiazolidin-4-one, and
5-(4-hydroxy-3-methoxy-benz-(Z)-ylidene)-2-[(Z)-propylimino]-3-(3-chlorophenyl)-thiazolidin-4-one.

Also especially preferred, the above processes are used to prepare compounds of Formula (II) selected from the group consisting of:
5-(3-chloro-4-hydroxy-benz-(Z)-ylidene)-2-[(Z)-isopropylimino]-3-phenyl-thiazolidin-4-one,
5-(4-hydroxy-benz-(Z)-ylidene)-2-[(Z)-propylimino]-3-phenyl-thiazolidin-4-one,
5-(3-chloro-4-hydroxy-benz-(Z)-ylidene)-2-[(Z)-propylmino]-3-phenyl-thiazolidin-4-one,
5-(4-hydroxy-3-methoxy-benz-(Z)-ylidene)-2-[(Z)-propylimino]-3-phenyl-thiazolidin-4-one,
5-(4-hydroxy-benz-(Z)-ylidene)-2-[(Z)-butylimino]-3-phenyl-thiazolidin-4-one,
5-(3-chloro-4-hydroxy-benz-(Z)-ylidene)-2-[(Z)-butylimino]-3-phenyl-thiazolidin-4-one,
5-(4-hydroxy-3-methoxy-benz-(Z)-ylidene)-2-[(Z)-butylimino]-3-phenyl-thiazolidin-4-one,
5-(3-chloro-4-hydroxy-benz-(Z)-ylidene)-2-[(Z)-isopropylimino]-3-(o-tolyl)-thiazolidin-4-one,
5-(4-hydroxy-benz-(Z)-ylidene)-2-[(Z)-propylimino]-3-(o-tolyl)-thiazolidin-4-one,
5-(3-chloro-4-hydroxy-benz-(Z)-ylidene)-2-[(Z)-propylimino]-3-(o-tolyl)-thiazolidin-4-one, and
5-(4-hydroxy-3-methoxy-benz-(Z)-ylidene)-2-[(Z)-propylimino]-3-(3-chlorophenyl)-thiazolidin-4-one.

In a further aspect the present invention relates to a compound of the Formula (II), wherein
$R^1$ represents phenyl which is optionally mono-, di- or tri-substituted wherein the substituents are independently selected from $C_{1-7}$-alkyl and halogen;
$R^2$ represents $C_{1-7}$-alkyl; and
$R^3$ represents hydrogen, hydroxy, $C_{1-7}$-alkoxy, or halogen.

In a preferred embodiment, the present invention relates to a compound of the Formula (II), wherein
$R^1$ represents phenyl which is optionally mono-substituted with $C_{1-7}$-alkyl (such as especially methyl) or halogen;
$R^2$ represents $C_{1-77}$-alkyl (such as especially propyl, isopropyl or butyl); and
$R^3$ represents hydrogen, $C_{1-7}$-alkoxy (such as especially methoxy), or halogen.

In an especially preferred embodiment, the present invention relates to a compound of the Formula (II), wherein $R^1$ represents phenyl which is optionally mono-substituted with methyl or chloro, $R^2$ represents propyl, isopropyl or butyl, and $R^3$ represents hydrogen, methoxy, or chloro.

In a more specific embodiment, the present invention relates to a compound of Formula (II) selected from the group consisting of:
5-(3-chloro-4-hydroxy-benz-(Z)-ylidene)-2-[(Z)-isopropylimino]-3-phenyl-thiazolidin-4-one,
5-(3-chloro-4-hydroxy-benz-(Z)-ylidene)-2-[(Z)-propylimino]-3-phenyl-thiazolidin-4-one,
5-(3-chloro-4-hydroxy-benz-(Z)-ylidene)-2-[(Z)-butylimino]-3-phenyl-thiazolidin-4-one,
5-(3-chloro-4-hydroxy-benz-(Z)-ylidene)-2-[(Z)-isopropylimino]-3-(o-tolyl)-thiazolidin-4-one,
5-(3-chloro-4-hydroxy-benz-(Z)-ylidene)-2-[(Z)-isopropylimino]-3-(3-chloro-phenyl)-thiazolidin-4-one,
5-(3-chloro-4-hydroxy-benz-(Z)-ylidene)-2-[(Z)-propylimino]-3-(o-tolyl)-thiazolidin-4-one,
5-(4-hydroxy-benz-(Z)-ylidene)-2-[(Z)-propylimino]-3-phenyl-thiazolidin-4-one,
5-(4-hydroxy-3-methoxy-benz-(Z)-ylidene)-2-[(Z)-propylimino]-3-phenyl-thiazolidin-4-one,
5-(4-hydroxy-benz-(Z)-ylidene)-2-[(Z)-butylimino]-3-phenyl-thiazolidin-4-one,
5-(4-hydroxy-3-methoxy-benz-(Z)-ylidene)-2-[(Z)-butylimino]-3-phenyl-thiazolidin-4-one,
5-(4-hydroxy-benz-(Z)-ylidene)-2-[(Z)-propylimino]-3-(o-tolyl)-thiazolidin-4-one, and
5-(4-hydroxy-3-methoxy-benz-(Z)-ylidene)-2-[(Z)-propylimino]-3-(3-chlorophenyl)-thiazolidin-4-one.

Compounds of Formula (II) described herein can be transformed into the compounds of General Formula (II) described in the patent application WO 2005/054215 using standard methods for the alkylation of phenols, like reaction in a solvent such as ethanol in the presence of a base such as sodium hydride, cesium carbonate, potassium carbonate or potassium tert-butoxide, with an appropriate alkyl halide, alkyl tosylate or alkyl triflate.

Any reference hereinbefore or hereinafter to a compound of Formula (I), Formula (II) or Structure 3 is to be understood as referring also to salts of such a compound, as appropriate and expedient.

The term $C_{1-7}$-alkyl as used herein means saturated, straight or branched chain groups with one to seven carbon atoms. $C_{1-7}$-alkyl as used for $R^2$ is preferably n-propyl, isopropyl or n-butyl.

The term $C_{1-7}$-alkoxy as used herein means an R—O— group, wherein R is $C_{1-7}$-alkyl.

The term halogen as used herein means fluoro, chloro, bromo or iodo, preferably chloro.

According to the invention, the compounds of Formulae (I) and (II) are manufactured by the methods given below. In general, they are prepared according to the general sequence of reactions outlined below in the General Reaction Scheme.

General Reaction Scheme:

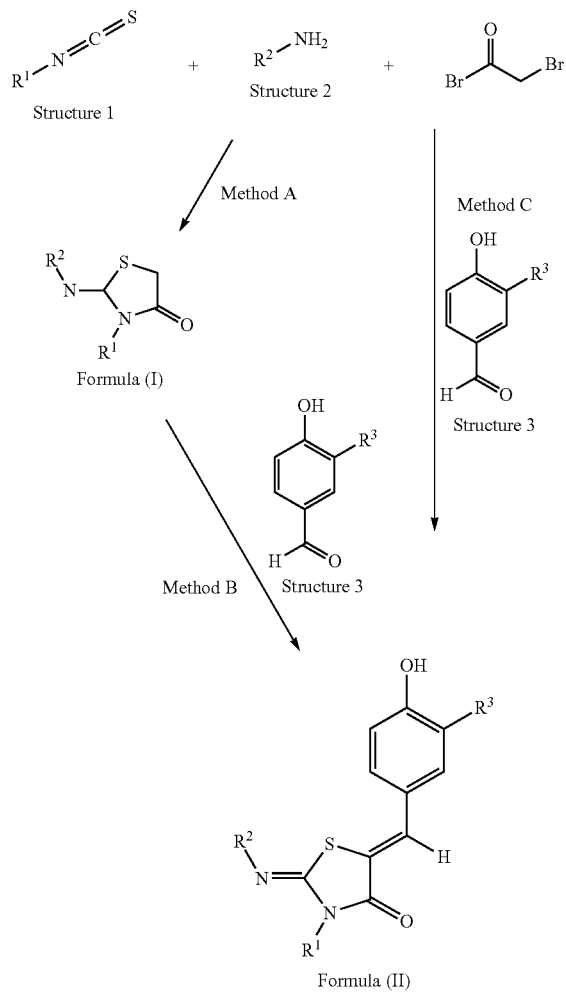

According to the General Reaction Scheme, compounds of the Formula (II) are prepared following Method B by reacting a compound of Formula (I) with a compound of Structure 3, for instance, in a solvent such as acetic acid at elevated temperatures and in the presence of a base such as sodium acetate. The required compounds of Formula (I) are prepared following Method A by reacting an isothiocyanate of Structure 1 successively with an amine of Structure 2, bromo-acetyl bromide and a pyridine base in a solvent such as dichloromethane. Alternatively, compounds of Formula (II) can be prepared following Method C without isolating and/or purifying the compounds of Formula (I), such that an isothiocyanate of Structure 1 is reacted successively with an amine of Structure 2, bromo-acetyl bromide and a pyridine base in a solvent such as dichloromethane, followed by the addition of an aldehyde of Structure 3, for instance, in a solvent such as acetic acid at elevated temperatures and in the presence of a base such as sodium acetate. The compounds of Structure 1, 2 and 3 are either commercially available or can be prepared according to procedures known to a person skilled in the art.

EXAMPLES

The following examples illustrate the invention.

All temperatures given are external temperatures and are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min, $t_R$ is given in minutes. Melting point is measured on Buchi melting point apparatus B540 and is not corrected.

Abbreviations:

DMSO dimethylsulfoxide h hour(s)

LC-MS liquid chromatography—mass spectrometry min minute(s)

m.p. melting point $t_R$ retention time

Typical procedure for the preparation of the 2-imino-thiazolidin-4-ones of Formula (I) (Method A)

To a solution of an arylisothiocyanate of Structure 1 (14.8 mmol) in dichloromethane (20 mL) is added portionwise an alkyl amine of Structure 2 (14.8 mmol) at 20° C. The solution is stirred at 20° C. for 15 min. The solution is cooled to 0° C. Bromo-acetyl bromide (1.287 mL, 14.8 mmol) is added carefully such that the temperature does not rise above 5° C. The reaction mixture is stirred at 0° C. for 15 min. To the reaction mixture is added pyridine (2.453 mL, 30.3 mmol) at 0° C. The mixture is stirred for another 15 min. The mixture is warmed to 20° C. The reaction mixture is washed with water (10 mL). The aqueous layer is extracted with dichloromethane (10 mL). The organic layers are combined and evaporated under reduced pressure to afford a 2-imino-thiazolidin-4-one of Formula (I).

Scaffold 1:

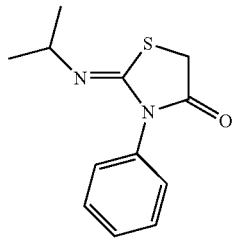
(I)a

2-[(Z)-Isopropylimino]-3-phenyl-thiazolidin-4-one is prepared as described in Method A. LC-MS: $t_R$=0.58 min, [M+1]$^+$=235; $^1$H-NMR (CDCl$_3$): δ 7.51-7.47 (m, 2H), 7.43-7.35 (m, 1H), 7.31-7.29 (m, 2H), 3.99 (s, 2H), 3.53 (hept, J=6.2 Hz, 1H), 1.15 (d, J=6.2 Hz, 6H); $^{13}$C-NMR (CDCl$_3$): δ 171.3, 135.2, 129.0, 128.5, 128.0, 125.8, 53.8, 32.6, 23.2.

Scaffold 2:

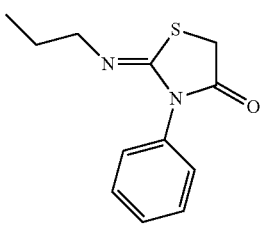
(I)b

3-Phenyl-2-[(Z)-propylimino]-thiazolidin-4-one is prepared as described in Method A. LC-MS: $t_R$=0.60 min, [M+1]$^+$=235; $^1$H-NMR (CDCl$_3$): δ 7.51-7.36 (m, 3H), 7.28-7.24 (m, 2H), 3.99 (s, 2H), 3.27 (t, J=7.0 Hz, 2H), 1.60 (hex, J=7.0 Hz, 2H), 0.91 (t, J=7.6 Hz, 3H); $^{13}$C-NMR (CDCl$_3$): δ 171.3, 135.1, 129.2, 128.7, 128.0, 121.0, 54.2, 32.7, 23.5, 11.8.

Scaffold 3:

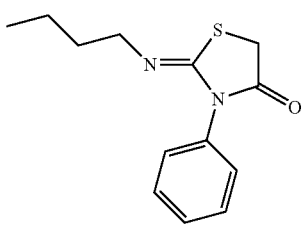
(I)c

2-[(Z)-n-Butylimino]-3-phenyl-thiazolidin-4-one is prepared as described in Method A. LC-MS: $t_R$=0.69 min, [M+1]$^+$=249; $^1$H-NMR (CDCl$_3$): δ 7.52-7.48 (m, 2H), 7.44-7.40 (m, 1H), 7.30-7.28 (m, 2H), 4.00 (s, 2H), 3.32 (t, J=7.0 Hz, 2H), 1.58 (p, 2H), 1.35 (sex, J$_1$=7.2, 2H), 0.93 (t, J=7.4 Hz, 3H); $^{13}$C-NMR (CDCl$_3$): δ 171.3, 135.1, 129.2, 128.7, 128.0, 121.0, 52.2, 32.7, 32.3, 20.5, 13.9.

Scaffold 4:

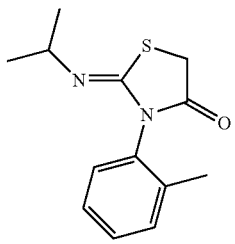
(I)d

2-[(Z)-Isopropylimino]-3-o-tolyl-thiazolidin-4-one is obtained following Method A. LC-MS: $t_R$=0.67 min, [M+1]$^+$=249; $^1$H-NMR (CDCl$_3$): δ 7.35-7.28 (m, 3H), 7.15-7.13 (m, 1H), 4.00 (s, 2H), 3.51 (hept, J=6.4 Hz, 1H), 2.18 (s, 3H), 1.12 (d, 3H), 1.11 (d, 3H); $^{13}$C-NMR (CDCl$_3$): δ 171.1, 136.1, 134.6, 131.1, 129.2, 128.6, 126.9, 53.9, 32.6, 23.4, 23.3, 17.6.

Scaffold 5:

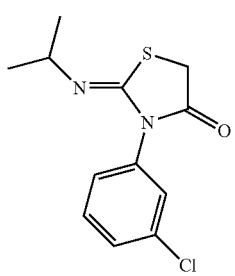
(I)e

2-[(Z)-Isopropylimino]-3-(3-chlorophenyl)-thiazolidin-4-one is prepared as described in Method A. LC-MS: $t_R$=0.76 min, [M+1]$^+$=269; $^1$H-NMR (CDCl$_3$): δ 7.43-7.20 (m, 4H), 3.98 (s, 2H), 3.51 (hept, J=6.2 Hz, 1H), 1.15 (d, 6H); $^{13}$C-NMR (CDCl$_3$): δ171.0, 136.2, 134.4, 129.9, 128.7, 128.5, 126.4, 53.9, 32.5, 23.3.

Scaffold 6:

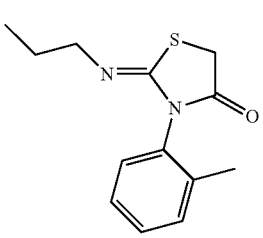
(I)f

2-[(Z)-Propylimino]-3-o-tolyl-thiazolidin-4-one is obtained following Method A. LC-MS: $t_R$=0.67 min, [M+1]$^+$=249; $^1$H-NMR (CDCl$_3$): δ 7.34-7.26 (m, 3H), 7.14-7.09 (m, 1H), 4.02 (s, 2H), 3.34-3.22 (m, 2H), 2.20 (s, 3H), 1.63-1.54 (m, 2H), 0.90 (t, J=7.4 Hz, 3H); $^{13}$C-NMR (CDCl$_3$): δ 171.1, 136.1, 134.5, 131.1, 129.4, 128.6, 127.1, 54.4, 32.6, 23.6, 17.6, 11.8.

TABLE 1

Summary of the results of the synthesis of the 2-imino-thiazolidin-4-ones of Formula (I)

| Scaffold | Compound | Yield [%] | Ratio of isomers[a] | Purity of compound of Formula (I) by LC-MS [area %][b] |
|---|---|---|---|---|
| 1 | (I)a | 79 | 95.0:5.0 | 78.5 |
| 2 | (I)b | 53 | 91.5:8.5 | 85.4 |
| 3 | (I)c | 74 | 93.0:7.0 | 89.0 |
| 4 | (I)d | 73 | 97.0:3.0 | 93.6 |
| 5 | (I)e | 77 | 96.6:3.4 | 90.1 |
| 6 | (I)f | 72 | 95.5:4.5 | 85.4 |

[a] Determined by $^1$H-NMR
[b] at 230 nm

The ratio of isomers as given in the above Table 1 refers to the ratio of the major regioisomer of Formula (I) to the minor regioisomer of Formula (III) as determined by $^1$H-NMR.

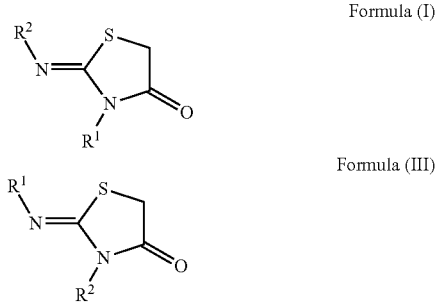

Formula (I)

Formula (III)

Typical Procedure for the Knoevenagel Condensation of Compounds of Formula (I) with Compounds of Structure 3 to Give Compounds of Formula (II) (Method B)

A solution of a 2-imino-thiazolidin-4-one of Formula (I) (4.27 mmol), a 4-hydroxy-benzaldehyde of Structure 3 (4.27 mmol) and sodium acetate (700 mg, 8.54 mmol) in acetic acid (10 mL) is stirred at 60° C. for 15 h. The suspension is cooled to 20° C. and filtered. The cake on the nutsche is washed with a mixture of water and acetic acid (5 mL, 1/1 [v]/[v]). The product is dried under reduced pressure.

Example 1

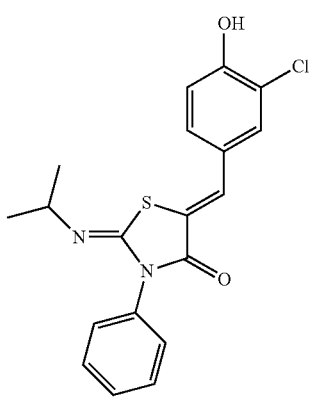

(II)a 5-(3-Chloro-4-hydroxy-benz-(Z)-ylidene)-2-[(Z)-isopropylimino]-3-phenyl-thiazolidin-4-one is obtained following Method B.

LC-MS: $t_R$=1.02 min, [M+1]$^+$=373;

$^1$H-NMR (deutero DMSO): δ 10.9 (s br, 1H), 7.68-7.65 (m, 2H), 7.52-7.49 (m, 3H), 7.45-7.35 (m, 3H), 7.15 (d, J=8.5 Hz, 1H), 3.55 (hept, J=6.2 Hz, 1H), 1.10 (d, J=6.2 Hz, 6H);

$^{13}$C-NMR (deutero DMSO): δ 8166.0, 155.2, 146.1, 135.9, 132.4, 130.4, 129.3, 128.9, 128.8, 126.3, 121.0, 119.1, 117.7, 54.8, 24.0;

m.p.: 270° C.

Example 2

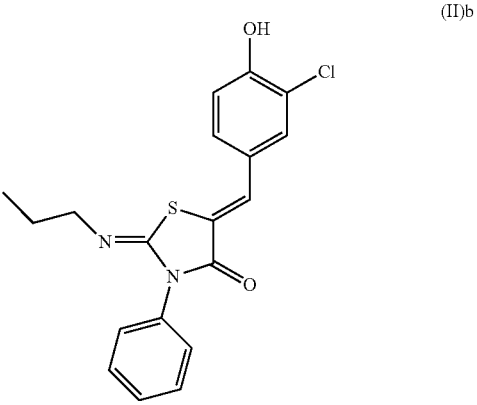 [SMILES: CCC/N=C1\S/C(=C\c2ccc(O)c(Cl)c2)C(=O)N1c1ccccc1]

(II)b 5-(3-Chloro-4-hydroxy-benz-(Z)-ylidene)-2-[(Z)-propylimino]-3-phenyl-thiazolidin-4-one is obtained following Method B.

LC-MS: $t_R$=1.01 min, [M+1]$^+$=373;

$^1$H-NMR (deutero DMSO): δ 10.2 (s br, 1H), 7.66 (s, 1H), 7.55-7.48 (m, 4H), 7.45-7.41 (m, 1H), 7.37-7.35 (m, 2H), 6.95 (d, J=8.3 Hz, 2H), 3.29 (t, J=6.8 Hz, 2H), 1.54 (hex, J=7.3, 2H), 0.86 (t, J=7.3 Hz, 3H);

$^{13}$C-NMR (deutero DMSO): δ 166.1, 155.2, 147.8, 135.9, 132.4, 130.3, 129.3, 128.9, 128.8, 126.3, 121.0, 119.2, 117.7, 54.7, 23.8, 12.2;

m.p.: 200° C.

Example 3

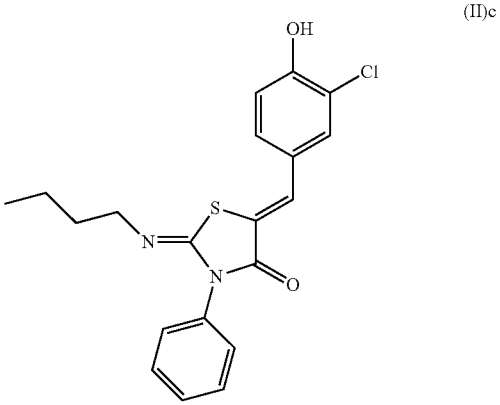 [SMILES: CCCC/N=C1\S/C(=C\c2ccc(O)c(Cl)c2)C(=O)N1c1ccccc1]

(II)c 5-(3-Chloro-4-hydroxy-benz-(Z)-ylidene)-2-[(Z)-butyl-imino]-3-phenyl-thiazolidin-4-one is obtained following Method B.

LC-MS: $t_R$=1.05 min, [M+1]$^+$=387;

$^1$H-NMR (deutero DMSO): δ 11.0 (s br, 1H), 7.69-7.66 (m, 2H), 7.52-7.48 (m, 3H), 7.45-7.41 (m, 1H), 7.37-7.35 (m, 2H), 7.15 (d, J=8.5 Hz, 1H), 3.33 (t, J=6.8 Hz, 2H), 1.54-1.46 (m, 2H), 1.34-1.25 (m, 2H), 0.87 (t, J=7.3 Hz, 3H);

$^{13}$C-NMR (deutero DMSO): δ 166.0, 155.4, 147.7, 135.9, 132.5, 130.3, 129.4, 128.95, 128.86, 128.2, 126.2, 121.0, 119.1, 117.7, 52.7, 32.7, 20.4, 14.2;

m.p.: 192° C.

Example 4

(II)d 5-(3-Chloro-4-hydroxy-benz-(Z)-ylidene)-2-[(Z)-isopropylimino]-3-(o-tolyl)-thiazolidin-4-one is obtained following Method B.

LC-MS: $t_R$=1.04 min, [M+1]$^+$=387;

$^1$H-NMR (deutero DMSO): δ 11.0 (s br, 1H), 7.70-7.66 (m, 2H), 7.53-7.51 (m, 1H), 7.38-7.25 (m, 4H), 7.15 (d, J=8.3 Hz, 1H), 3.55 (hept, J=6.0 Hz, 1H), 2.08 (s, 3H), 1.10 (d, J=5.9 Hz, 3H), 1.08 (d, 3H);

$^{13}$C-NMR (deutero DMSO): δ 165.8, 155.3, 145.3, 136.3, 135.2, 132.5, 131.1, 130.4, 129.50, 129.46, 129.0, 127.3, 126.2, 121.1, 119.0, 117.7, 54.9, 24.1, 24.0, 17.6;

m.p.: 252° C.

Example 5

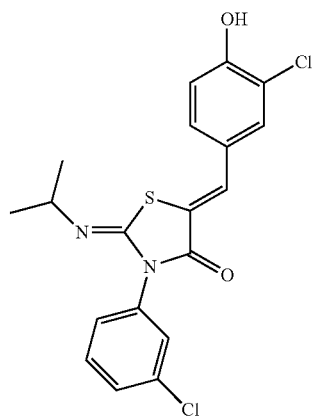

(II)e 5-(3-Chloro-4-hydroxy-benz-(Z)-ylidene)-2-[(Z)-isopropylimino]-3-(3-chloro-phenyl)-thiazolidin-4-one is obtained following Method B.

LC-MS: $t_R$=1.07 min, [M+1]$^+$=407;

$^1$H-NMR (deutero DMSO): δ 11.0 (s br, 1H), 7.68-7.67 (m, 2H), 7.56-7.49 (m, 4H), 7.39-7.37 (m, 1H), 7.15 (d, J=8.3 Hz, 1H), 3.55 (hept, J=6.0 Hz, 1H), 1.10 (d, J=6.5 Hz, 3H);

$^{13}$C-NMR (deutero DMSO): δ 165.9, 155.5, 145.9, 137.2, 133.3, 132.5, 130.9, 130.4, 129.05, 129.01, 128.9, 127.9, 126.1, 121.1, 118.8, 117.8, 54.8, 24.0;

m.p.: 272° C.

Example 6

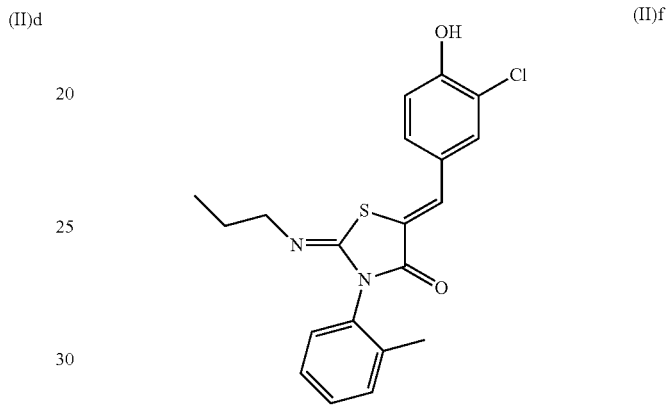

(II)f 5-(3-Chloro-4-hydroxy-benz-(Z)-ylidene)-2-[(Z)-propy-limino]-3-(o-tolyl)-thiazolidin-4-one is obtained following Method B.

LC-MS: $t_R$=1.03 min, [M+1]$^+$=387;

$^1$H-NMR (deutero DMSO): δ 11.0 (s br, 1H), 7.70-7.67 (m, 2H), 7.53-7.51 (m, 1H), 7.38-7.25 (m, 4H), 7.15 (d, J=8.3 Hz, 1H), 3.36-3.24 (m, 2H), 2.09 (s, 3H), 1.56-1.47 (m, 2H), 0.84 (t, J=7.3 Hz, 3H);

$^{13}$C-NMR (deutero DMSO): δ 165.8, 155.3, 147.0, 136.3, 135.2, 132.5, 131.1, 130.3, 129.53, 129.50, 129.0, 127.3, 126.2, 121.1, 119.0, 117.8, 54.8, 23.9, 17.6, 12.2;

m.p.: 199° C.

TABLE 2

Summary of the results of the Knoevenagel reactions yielding compounds of Formula (II), following Method B

| Example | Compound | Yield [%] | Purity of compound of Formula (II) by LC-MS [area %]$^{a)}$ |
|---|---|---|---|
| 1 | (II)a | 71 | 100 |
| 2 | (II)b | 77 | 100 |
| 3 | (II)c | 84 | 100 |
| 4 | (II)d | 73 | 100 |
| 5 | (II)e | 60 | 100 |
| 6 | (II)f | 69 | 100 |

$^{a)}$at 254 nm

Typical One-Pot Procedure for the Preparation of the Knoevenagel Products of Formula (II) (Method C)

To a solution of an arylisothiocyanate of Structure 1 (14.8 mmol) in dichloromethane (20 mL) is added portionwise an alkyl amine of Structure 2 (14.8 mmol) at 20° C. The solution is stirred at 20° C. for 15 min. The solution is cooled to 0° C. Bromo-acetyl bromide (1.287 mL, 14.8 mmol) is added carefully such that the temperature does not rise above 5° C. The reaction mixture is stirred at 0° C. for 15 min. To the reaction mixture is added pyridine (2.453 mL, 30.3 mmol) at 0° C. The mixture is stirred for another 15 min. The mixture is warmed to 20° C. An in-process control is performed to determine the ratio of the regioisomers of Formula (I) and (III). Dichloromethane is removed under reduced pressure. To the residue is added a 4-hydroxy-benzaldehyde of Structure 3 (14.8 mmol), sodium acetate (2.427 g, 29.6 mmol) and acetic acid (20 mL). The reaction mixture is stirred at 60° C. for 15 h. The suspension is cooled to 20° C. and water (20 mL) is added. The suspension is filtered. The cake on the nutsche is washed with a mixture of water and acetic acid (10 mL, 1/1 [v]/[v]). The product is dried under reduced pressure.

In an alternative Method C', the same procedure is followed as described for Method C above, except for the following variations: The major part of dichloromethane is removed at ambient pressure at elevated temperatures (55-65° C.). Instead of cooling the suspension to 20° C. and adding water after the reaction with the benzaldehyde of Structure 3, more solvent is removed under reduced pressure and 75-85° C., and water (20 mL) is added at 60° C. The suspension is then filtered and the cake on the nutsche is washed with a mixture of water and acetic acid (10 mL), optionally followed by a wash with water (10 mL). The product is then dried under reduced pressure at 20-75° C.

Example 7

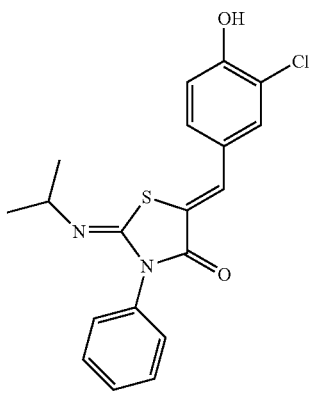

(II)a 5-(3-Chloro-4-hydroxy-benz-(Z)-ylidene)-2-[(Z)-isopropylimino]-3-phenyl-thiazolidin-4-one is obtained following Method C.

For analytical data see Example 1.

Example 8

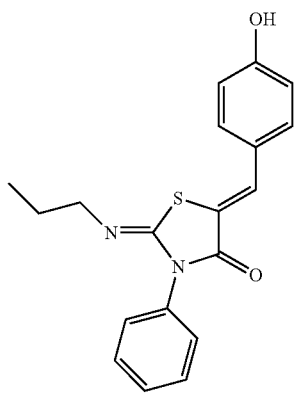

(II)g 5-(4-Hydroxy-benz-(Z)-ylidene)-2-[(Z)-propylimino]-3-phenyl-thiazolidin-4-one is obtained following Method C.

LC-MS: $t_R$=0.93 min, [M+1]$^+$=339;

$^1$H-NMR (deutero DMSO): δ 10.2 (s br, 1H), 7.66 (s, 1H), 7.55-7.48 (m, 4H), 7.45-7.41 (m, 1H), 7.37-7.35 (m, 2H), 6.95 (d, J=8.3 Hz, 2H), 3.29 (t, J=6.8 Hz, 2H), 1.54 (hex, J=7.3, 2H), 0.86 (t, J=7.3 Hz, 3H);

$^{13}$C-NMR (deutero DMSO): δ 166.3, 159.9, 148.2, 136.0, 132.6, 130.3, 129.3, 129.0, 128.8, 125.0, 117.3, 116.8, 54.6, 23.8, 12.2;

m.p.: 232° C.

Example 9

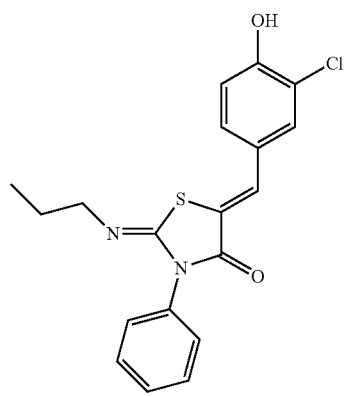

(II)b 5-(3-Chloro-4-hydroxy-benz-(Z)-ylidene)-2-[(Z)-propylimino]-3-phenyl-thiazolidin-4-one is obtained following Method C.

For analytical data see Example 2.

Example 10

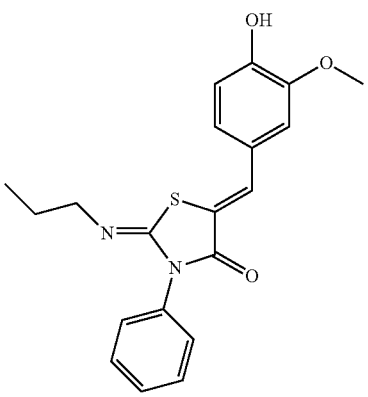

(II)h 5-(4-Hydroxy-3-methoxy-benz-(Z)-ylidene)-2-[(Z)-propylimino]-3-phenyl-thiazolidin-4-one is obtained following Method C.

LC-MS: $t_R$=0.95 min, [M+1]$^+$=369;

$^1$H-NMR (deutero DMSO): δ 9.84 (s br, 1H), 7.69 (s, 1H), 7.53-7.49 (m, 2H), 7.45-7.42 (m, 1H), 7.38-7.36 (m, 2H), 7.26 (s, 1H), 7.16 (d, J=7.8 Hz, 1H), 6.97 (d, J=8.3 Hz, 1H), 3.84 (s, 3H), 3.30 (t, J=6.8 Hz, 2H), 1.54 (hex, J=7.3, 2H), 0.86 (t, J=7.3 Hz, 3H);

$^{13}$C-NMR (deutero DMSO): δ166.2, 149.4, 148.4, 135.9, 130.7, 129.4, 129.0, 128.8, 125.4, 123.9, 121.0, 117.5, 116.7, 115.1, 56.2, 54.5, 23.8, 12.2;

m.p.: 173° C.

Example 11

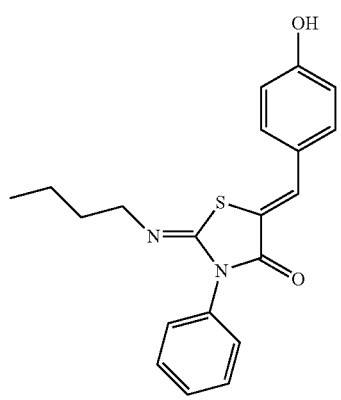

(II)i 5-(4-Hydroxy-benz-(Z)-ylidene)-2-[(Z)-butylimino]-3-phenyl-thiazolidin-4-one is obtained following Method C.

LC-MS: $t_R$=0.98 min, [M+1]$^+$=353;

$^1$H-NMR (deutero DMSO): δ 10.2 (s br, 1H), 7.67 (s, 1H), 7.55-7.48 (m, 4H), 7.44-7.41 (m, 1H), 7.37-7.35 (m, 2H), 6.95 (d, J=8.3 Hz, 2H), 3.33 (t, J=6.8 Hz, 2H), 1.54-1.47 (m, 2H), 1.34-1.25 (m, 2H), 0.87 (t, J=7.3 Hz, 3H);

$^{13}$C-NMR (deutero DMSO): δ166.3, 159.9, 148.1, 136.0, 132.6, 130.3, 129.3, 129.0, 128.8, 125.0, 117.3, 116.7, 52.7, 32.7, 20.4, 14.2;

m.p.: 228° C.

Example 12

Example 13

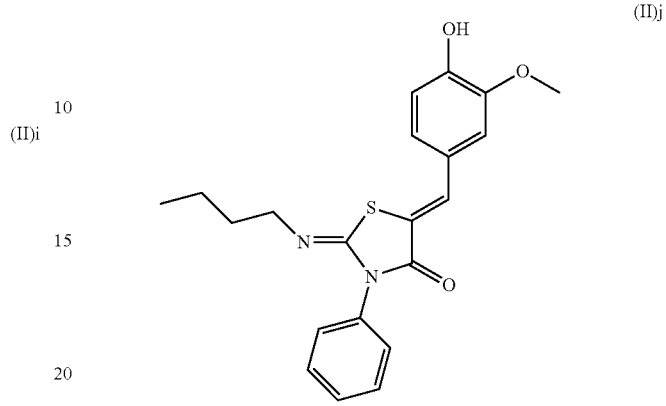

(II)j 5-(4-Hydroxy-3-methoxy-benz-(Z)-ylidene)-2-[(Z)-butylimino]-3-phenyl-thiazolidin-4-one is obtained following Method C.

LC-MS: $t_R$=0.99 min, [M+1]$^+$=383;

$^1$H-NMR (deutero DMSO): δ 9.86 (s br, 1H), 7.68 (s, 1H), 7.52-7.49 (m, 2H), 7.45-7.41 (m, 1H), 7.37-7.35 (m, 2H), 7.26 (s, 1H), 7.15 (d, J=8.3 Hz, 1H), 6.97 (d, J=8.3 Hz, 1H), 3.84 (s, 3H), 3.34 (t, J=6.8 Hz, 2H), 1.54-1.46 (m, 2H), 1.34-1.25 (m, 2H), 0.87 (t, J=7.3 Hz, 3H);

$^{13}$C-NMR (deutero DMSO): δ 166.2, 149.4, 148.4, 148.1, 136.0, 130.6, 129.3, 129.0, 128.8, 125.5, 123.9, 117.5, 116.7, 115.1, 56.2, 52.6, 32.6, 20.3, 14.2;

m.p.: 164° C.

Example 14

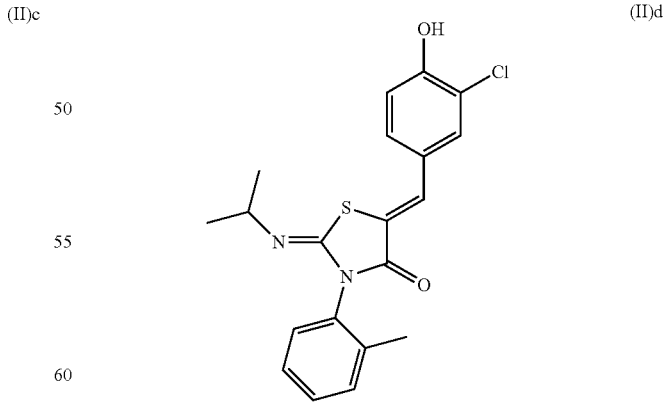

(II)c 5-(3-Chloro-4-hydroxy-benz-(Z)-ylidene)-2-[(Z)-butylimino]-3-phenyl-thiazolidin-4-one is obtained following Method C.

For analytical data see Example 3.

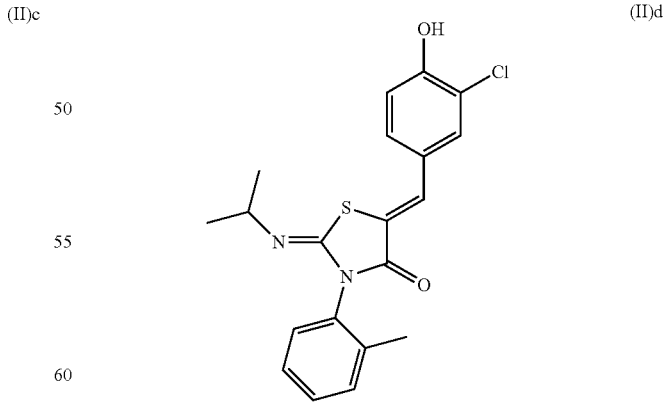

(II)d 5-(3-Chloro-4-hydroxy-benz-(Z)-ylidene)-2-[(Z)-isopropylimino]-3-(o-tolyl)-thiazolidin-4-one is obtained following Method C.

For analytical data see Example 4.

Example 15

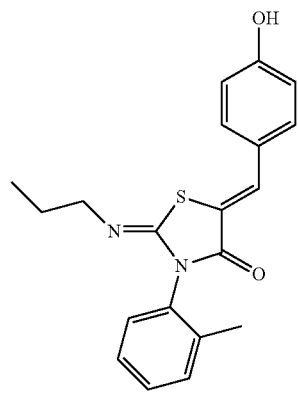

(II)k 5-(4-Hydroxy-benz-(Z)-ylidene)-2-[(Z)-propylimino]-3-(o-tolyl)-thiazolidin-4-one is obtained following Method C.

LC-MS: $t_R$=0.97 min, [M+1]$^+$=353;

$^1$H-NMR (deutero DMSO): δ 11.1 (s br, 1H), 7.67 (s, 1H), 7.55-7.54 (m, 2H), 7.38-7.24 (m, 4H), 6.95 (d, J=8.3 Hz, 2H), 3.36-3.24 (m, 2H), 2.09 (s, 3H), 1.56-1.47 (m, 2H), 0.84 (t, J=7.3 Hz, 3H);

$^{13}$C-NMR (deutero DMSO): δ166.0, 159.9, 147.5, 136.3, 135.3, 132.7, 131.1, 130.4, 129.6, 129.4, 127.3, 124.9, 117.2, 116.8, 54.7, 23.9, 17.6, 12.2;

m.p.: 198° C.

Example 16

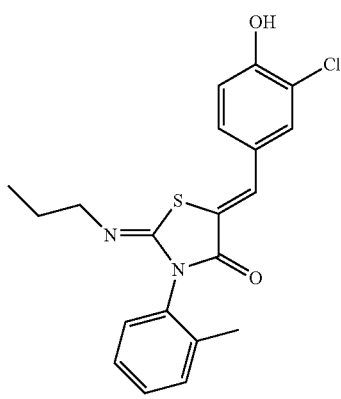

(II)f 5-(3-Chloro-4-hydroxy-benz-(Z)-ylidene)-2-[(Z)-propylimino]-3-(o-tolyl)-thiazolidin-4-one is obtained following Method C.

For analytical data see Example 6.

Example 17

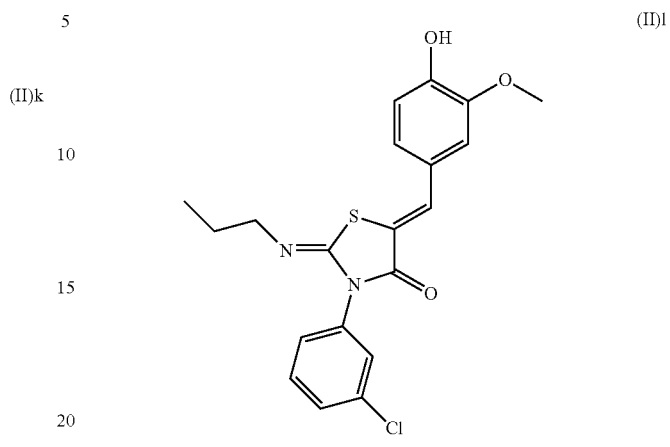

(II)l 5-(4-Hydroxy-3-methoxy-benz-(Z)-ylidene)-2-[(Z)-propylimino]-3-(3-chlorophenyl)-thiazolidin-4-one is obtained following Method C.

LC-MS: $t_R$=1.02 min, [M+1]$^+$=403;

$^1$H-NMR (deutero DMSO): δ 9.86 (s br, 1H), 7.69 (s, 1H), 7.56-7.50 (m, 3H), 7.40-7.37 (m, 1H), 7.26 (s, 1H), 7.16 (d, J=8.5 Hz, 1H), 6.97 (d, J=7.5 Hz, 1H), 3.85 (s, 3H), 3.30 (t, J=6.9 Hz, 2H), 1.59-1.50 (m, 2H), 0.87 (t, J=7.4 Hz, 3H);

$^{13}$C-NMR (deutero DMSO): δ166.0, 149.5, 148.4, 148.0, 137.2, 133.3, 130.86, 130.80, 129.1, 128.9, 128.0, 125.4, 123.9, 117.5, 116.7, 115.2, 56.2, 54.5, 23.9, 12.2;

m.p.: 200° C.

TABLE 3

Results of the one-pot procedure yielding compounds of Formula (II) following Method C

| Example | Compound | Yield [%] | Ratio of isomers of intermediates of Formula (I) and (III)[a] | Purity of compound of Formula (II) by LC-MS [area %][b] |
|---|---|---|---|---|
| 7 | (II)a | 88 | 97:3 | 100 |
| 8 | (II)g | 80 | 94:6 | 100 |
| 9 | (II)b | 80 | 94:6 | 89.0 |
| 10 | (II)h | 96 | 93:7 | 100 |
| 11 | (II)i | 82 | 94:6 | 100 |
| 12 | (II)c | 86 | 94:6 | 97 |
| 13 | (II)j | 84 | 94:6 | 76 |
| 14 | (II)d | 83 | 96:4 | 100 |
| 15 | (II)k | 78 | 97:3 | 94 |
| 16 | (II)f | 84 | 97:3 | 98 |
| 17 | (II)l | 84 | 95:5 | 100 |

[a] Determined by LC-MS at 250 nm after addition of pyridine, prior to the solvent change to acetic acid.
[b] at 254 nm The ratio of isomers as given in the above Table 3 refers to the ratio of the major regioisomer of Formula (I) to the minor regioisomer of Formula (III), said isomers occurring as intermediates in the preparation of compounds of Formula (II). The ratio of the isomers is determined by LC-MS in an in-process control.

Table 4 below shows the regioselectivity of the 2-iminothiazolidin-4-one scaffold synthesis performed according to Method A of WO 2005/054215 (WO 2005/054215 is hereinafter referred to as D1) compared to Method A of the present invention. The ratios of the regioisomers in the reaction mixtures (i.e. before the work-up procedure) are determined according to the methods indicated in the table.

TABLE 4

Regioselectivity of the 2-imino-thiazolidin-4-one scaffold synthesise[a]

$R_1$—NCS

+

$R_2$—$NH_2$ $R_2$ = isopropyl 2a-f
$R_2$ = n-propyl 4a-f

A

B 3a-f
5a-f

| $R_2$ | | isopropyl | | n-propyl | |
|---|---|---|---|---|---|
| Method | | Method A of D1 | Method A of present invention | Method A of D1 | Method A of present invention |
| R | | $OCH_3$ | Br | $OCH_3$ | Br |
| $R_1$ | x | 2x:3x | 2x:3x | 4x:5x | 4x:5x |
| phenyl | a | 11:1[b] | 26:1 | 1:8 | 25:1 |
| 2-methyl-phenyl | b | 4:1 | 42:1[g] | 1:10 | 41:1 |
| 3-methyl-phenyl | c | 13:1 | 63:1 | 1:8 | 34:1 |
| 4-methyl-phenyl | d | 18:1 | 54:1 | 1:7 | 28:1 |
| 2,6-dimethyl-phenyl | e | 1:13[f] | 18:1 | 1:100[c] | 21:1[d] |
| 2-chloro-phenyl | f | 3:1 | 47:1 | 1:24[e] | 47:1 |

[a]Regio-isomer ratios A:B as assessed by LC-MS run under acidic conditions (Zorbax SB-AQ column, 5 μm, 120 Å, 4.6 × 50 mm (Agilent), gradient: 5-95% acetonitrile in water containing 0.04% of trifluoroacetic acid, within 1 min, flow: 4.5 mL/min) at 230 nm; the following ratios have also been determined by $^1$H NMR analysis of the crude reaction mixtures:
[b]10:1;
[c]1:42;
[d]15:1;
[e]1:19;
[f]ratio determined by $^1$H NMR only;
[g]ratio determined using LC-MS run under basic conditions (Zorbax Extend C18 column, 5 μm, 80 Å, 4.6 × 50 mm (Agilent), eluting with a gradient of 5-95% of acetonitrile in water containing 13 mM of $NH_3$).

Table 4 shows that the use of Method A of the present invention leads to a significant improvement with regard to regioselectivity towards the desired regioisomer A when compared to Method A of D1.

The potential effect of the base on regioselectivity has also been investigated. In order to do so, 1-propyl-3-o-tolyl-thiourea, which was obtained by reacting o-tolyl-isothiocyanate with n-propylamine, was treated with one equivalent of bromo-acetyl bromide in dichloromethane. After stirring for 5 minutes two equivalents of either triethylamine or pyridine were added. After stirring for further 5 minutes, a sample was taken and analysed by LC-MS. The analysis showed a conversion of 100% and a ratio of the 2-propylimino-3-o-tolyl-thiazolidin-4-one isomer to the 3-propyl-2-o-tolylimino-thiazolidin-4-one isomer of 81:19 for triethylamine and 97:3 for pyridine. This shows that the nature of the base has an influence on regioselectivity and that pyridine is superior to triethylamine.

The invention claimed is:

1. A process for the preparation of a compound of the Formula (I):

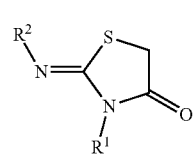

Formula (I)

wherein
R[1] represents phenyl which is optionally mono-, di- or tri-substituted wherein the substituents are independently selected from $C_{1-7}$-alkyl and halogen; and
R[2] represents $C_{1-7}$-alkyl;
which process comprises reacting a compound of the formula R[1]—N═C═S, wherein R[1] is as defined for Formula (I), with a compound of the formula R[2]—$NH_2$, wherein R[2] is as defined for Formula (I), followed by reaction with bromo-acetyl bromide and a pyridine base in the presence of the solvent dichloromethane.

2. The process according to claim 1, wherein no isolation and/or purification of intermediates occurs.

3. The process according to claim 1, wherein the pyridine base is pyridine.

4. The process according to claim 1, wherein R[1] represents phenyl which is optionally mono-substituted with $C_{1-7}$-alkyl or halogen, and R[2] represents $C_{1-7}$-alkyl.

5. The process according to claim 4, wherein R[1] represents phenyl which is optionally mono-substituted with methyl or chloro, and R[2] represents propyl, isopropyl or butyl.

6. The process according to claim 1 for preparing a compound selected from the group consisting of:
2-[(Z)-isopropylimino]-3-phenyl-thiazolidin-4-one,
3-phenyl-2-[(Z)-propylimino]-thiazolidin-4-one,
2-[(Z)-n-butylimino]-3-phenyl-thiazolidin-4-one,
2-[(Z)-isopropylimino]-3-o-tolyl-thiazolidin-4-one,
2-[(Z)-isopropylimino]-3-(3-chlorophenyl)-thiazolidin-4-one, and
2-[(Z)-propylimino]-3-o-tolyl-thiazolidin-4-one.

7. A process for the preparation of a compound of Formula (II):

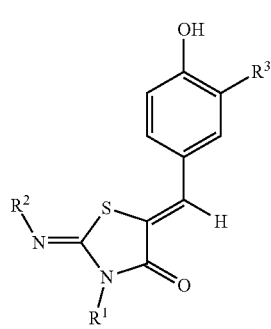

Formula (II)

wherein
R[1] represents phenyl which is optionally mono-, di- or tri-substituted wherein the substituents are independently selected from $C_{1-7}$-alkyl and halogen;
R[2] represents $C_{1-7}$-alkyl; and
R[3] represents hydrogen, hydroxy, $C_{1-7}$-alkoxy, or halogen;

which process comprises preparing a compound of Formula (I) according to the process of claim 1 and reacting such compound of Formula (I) with a compound of Structure 3:

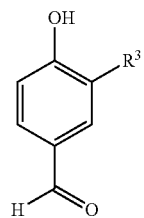

wherein $R^3$ is as defined for Formula (II) above.

8. The process according to claim 7, wherein the compound of Formula (I) is reacted with the compound of Structure 3 in the presence of acetic acid and a base, at elevated temperatures.

9. A process for the preparation of a compound of the Formula (II) according to claim 7, which process comprises reacting a compound of the formula $R^1$—N═C═S, wherein $R^1$ represents phenyl which is optionally mono-, di- or tri-substituted wherein the substituents are independently selected from $C_{1-7}$-alkyl and halogen, with a compound of the formula $R^2$—$NH_2$, wherein $R^2$ represents $C_{1-7}$-alkyl, followed by reaction with bromo-acetyl bromide and a pyridine base, to obtain a compound of Formula (I):

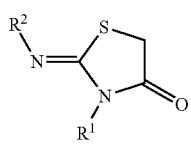

wherein $R^1$ represents phenyl which is optionally mono-, di- or tri-substituted wherein the substituents are independently selected from $C_{1-7}$-alkyl and halogen; and $R^2$ represents $C_{1-7}$-alkyl;

followed by reaction with a compound of Structure 3, wherein $R^3$ is as defined in claim 7, characterized in that the compound of Formula (I) is not isolated and/or purified.

10. The process according to claim 9, wherein the preparation of the compound of Formula (I) occurs in the presence of dichloromethane, followed by a solvent change in order that the reaction with a compound of Structure 3 occurs in the solvent acetic acid and in the presence of a base, at elevated temperatures.

11. The process according to claim 9, wherein the pyridine base is pyridine.

12. The process according to claim 7, wherein $R^1$ represents phenyl which is optionally mono-substituted with $C_{1-7}$-alkyl or halogen, $R^2$ represents $C_{1-7}$-alkyl, and $R^3$ represents hydrogen, $C_{1-7}$-alkoxy, or halogen.

13. The process according to claim 12, wherein $R^1$ represents phenyl which is optionally mono-substituted with methyl or chloro, $R^2$ represents propyl, isopropyl or butyl, and $R^3$ represents hydrogen, methoxy, or chloro.

14. The process according to claim 7 for preparing a compound selected from the group consisting of:

5-(3-chloro-4-hydroxy-benz-(Z)-ylidene)-2-[(Z)-isopropylimino]-3-phenyl-thiazolidin-4-one, 5-(3-chloro-4-hydroxy-benz-(Z)-ylidene)-2-[(Z)-propylimino]-3-phenyl-thiazolidin-4-one, 5-(3-chloro-4-hydroxy-benz-(Z)-ylidene)-2-[(Z)-butylimino]-3-phenyl-thiazolidin-4-one, 5-(3-chloro-4-hydroxy-benz-(Z)-ylidene)-2-[(Z)-isopropylimino]-3-(o-tolyl)-thiazolidin-4-one, 5-(3-chloro-4-hydroxy-benz-(Z)-ylidene)-2-[(Z)-isopropylimino]-3-(3-chloro-phenyl)-thiazolidin-4-one, 5-(3-chloro-4-hydroxy-benz-(Z)-ylidene)-2-[(Z)-propylimino]-3-(o-tolyl)-thiazolidin-4-one, 5-(4-hydroxy-benz-(Z)-ylidene)-2-[(Z)-propylimino]-3-phenyl-thiazolidin-4-one, 5-(4-hydroxy-3-methoxy-benz-(Z)-ylidene)-2-[(Z)-propylimino]-3-phenyl-thiazolidin-4-one, 5-(4-hydroxy-benz-(Z)-ylidene)-2-[(Z)-butylimino]-3-phenyl-thiazolidin-4-one, 5-(4-hydroxy-3-methoxy-benz-(Z)-ylidene)-2-[(Z)-butylimino]-3-phenyl-thiazolidin-4-one, 5-(4-hydroxy-benz-(Z)-ylidene)-2-[(Z)-propylimino]-3-(o-tolyl)-thiazolidin-4-one, and 5-(4-hydroxy-3-methoxy-benz-(Z)-ylidene)-2-[(Z)-propylimino]-3-(3-chlorophenyl)-thiazolidin-4-one.

15. The process according to claim 7 for preparing a compound selected from the group consisting of:

5-(3-chloro-4-hydroxy-benz-(Z)-ylidene)-2-[(Z)-isopropylimino]-3-phenyl-thiazolidin-4-one, 5-(4-hydroxy-benz-(Z)-ylidene)-2-[(Z)-propylimino]-3-phenyl-thiazolidin-4-one, 5-(3-chloro-4-hydroxy-benz-(Z)-ylidene)-2-[(Z)-propylimino]-3-phenyl-thiazolidin-4-one, 5-(4-hydroxy-3-methoxy-benz-(Z)-ylidene)-2-[(Z)-propylimino]-3-phenyl-thiazolidin-4-one, 5-(4-hydroxy-benz-(Z)-ylidene)-2-[(Z)-butylimino]-3-phenyl-thiazolidin-4-one, 5-(3-chloro-4-hydroxy-benz-(Z)-ylidene)-2-[(Z)-butylimino]-3-phenyl-thiazolidin-4-one, 5-(4-hydroxy-3-methoxy-benz-(Z)-ylidene)-2-[(Z)-butylimino]-3-phenyl-thiazolidin-4-one, 5-(3-chloro-4-hydroxy-benz-(Z)-ylidene)-2-[(Z)-isopropylimino]-3-(o-tolyl)-thiazolidin-4-one, 5-(4-hydroxy-benz-(Z)-ylidene)-2-[(Z)-propylimino]-3-(o-tolyl)-thiazolidin-4-one, 5-(3-chloro-4-hydroxy-benz-(Z)-ylidene)-2-[(Z)-propylimino]-3-(o-tolyl)-thiazolidin-4-one, and 5-(4-hydroxy-3-methoxy-benz-(Z)-ylidene)-2-[(Z)-propylimino]-3-(3-chlorophenyl)-thiazolidin-4-one.

16. The process according to claim 1 for preparing 2-[(Z)-propylimino]-3-o-tolyl-thiazolidin-4-one.

17. The process according to claim 7 for preparing 5-(3-chloro-4-hydroxy-benz-(Z)-ylidene)-2-[(Z)-propylimino]-3-(o-tolyl)-thiazolidin-4-one.

18. A process for the preparation of a compound of the Formula (III):

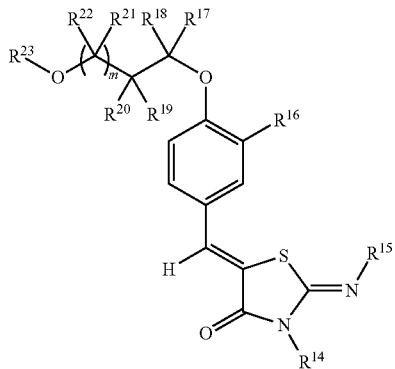

Formula (III)

wherein $R^{14}$ represents phenyl which is optionally mono-, di- or tri-substituted wherein the substituents are independently selected from $C_{1-7}$-alkyl and halogen;

$R^{15}$ represents $C_{1-7}$-alkyl;

$R^{16}$ represents hydrogen, hydroxy, $C_{1-7}$-alkoxy, or halogen;

$R^{17}$ represents hydrogen, lower alkyl, or hydroxymethyl;

$R^{18}$, $R^{19}$, $R^{21}$ and $R^{22}$ each represents independently hydrogen or methyl;

$R^{20}$ represents hydrogen or lower alkyl, and in case m represents the integer 1, $R^{20}$ in addition represents lower alkoxy, hydroxy, —$NH_2$, —$NHR^5$ or —$NR^5R^6$, wherein $R^5$ and $R^6$ each represents independently lower alkyl;

$R^{23}$ represents hydrogen, lower alkyl, hydroxycarbonyl-lower alkyl, 1-glyceryl, or 2-glyceryl; and m represents the integer 0 or 1;

or a pharmaceutically acceptable salt thereof;

and wherein the terms "lower alkyl" and "lower alkoxy" have the following meanings:

"lower alkyl", alone or in combination with other groups, means saturated, straight or branched chain groups with one to seven carbon atoms; and "lower alkoxy" means an R—O group, wherein R is a lower alkyl;

which process comprises reacting a compound of the formula $R^{14}$—N=C=S, wherein $R^{14}$ is as defined for Formula (III), with a compound of the formula $R^{15}$—NH2, wherein $R^{15}$ is as defined for Formula (III), followed by reaction with bromo-acetyl bromide and a pyridine base in the presence of the solvent dichloromethane.

19. The process according to claim 18, wherein the pyridine base is pyridine.

* * * * *